US006835867B1

(12) United States Patent
Woychik et al.

(10) Patent No.: US 6,835,867 B1
(45) Date of Patent: Dec. 28, 2004

(54) ALLELIC SERIES OF GENOMIC MODIFICATIONS IN CELLS

(76) Inventors: Richard P. Woychik, 107 Bates Ct., Orinda, CA (US) 94563; Terry R. Magnuson, 408 Bayberry Dr., Chapel Hill, NC (US) 27514; Ellis D. Avner, 25485 Penshurst Dr., Beachwood, OH (US) 44122; James W. Thomas, 5711 Wainwright Ave., Rockville, MD (US) 20851

( * ) Notice: Subject to any disclaimer, the term of this patent is extended or adjusted under 35 U.S.C. 154(b) by 0 days.

(21) Appl. No.: 09/103,846

(22) Filed: Jun. 24, 1998

(51) Int. Cl.$^7$ .................. C12N 15/00; C12N 15/09; C12N 5/00

(52) U.S. Cl. ................ 800/21; 800/8; 800/14; 800/18; 800/20; 800/22; 435/441; 435/442; 435/443; 435/444; 435/445; 435/446; 435/447; 435/448; 435/455; 435/462; 435/463; 435/325

(58) Field of Search .................. 800/14, 18, 20–22, 800/8; 435/441, 442, 443, 444, 445, 446, 447, 448, 455, 462, 463, 325

(56) References Cited

U.S. PATENT DOCUMENTS

| | | | | |
|---|---|---|---|---|
| 4,683,195 A | | 7/1987 | Mullis et al. ............... | 435/6 |
| 4,683,202 A | | 7/1987 | Mullis ....................... | 435/91 |
| 4,965,188 A | | 10/1990 | Mullis et al. ............... | 435/6 |
| 6,015,670 A | * | 1/2000 | Goodfellow ................ | 435/6 |
| 6,033,861 A | * | 3/2000 | Schafer et al. ............. | 435/6 |

OTHER PUBLICATIONS

Moreadith et al., Journal of Molecular Medicine, vol. 75, pp. 208–216, 1997.*
Seamark, Reproduction, Fertility and Development, vol. 6, No. 5, pp. 653–657, 1994.*
Mullins et al., Journal of Clinical Investigations, vol. 98, No. 11, pp. S37–S40, 1996.*
Thomas et al., PNAS of the USA, vol. 95, No. 3, pp. 1114–1119, Feb. 3, 1998.*
Cohen–Tannoudji et al., Molecular and Cellular Biology, vol. 18, No. 3, pp. 1444–1448, Mar. 1998.*
Slamenova et al., Mutation Research, vol. 383, pp. 243–252, 1997.*
Cohen–Tannoudji et al. (1998) "I–Scel–Induced Gene Replacement at a Natural Locus in Embryonic Stem Cells," Mol. Cell. Biol. 18:1444–1448.
Dobrovolsky et al. (1996) "Development of Novel Mouse tk+/– Embryonic stem cell line for use in mutagenicity studies," Environmental and Molecular Mutagenesis 28:483–489.
Sehlmeyer et al. (1994) "Lower mutation frequencies are induced by ENU in undifferentiated embryonic cells than in differentiated cells of the mouse in vitro," Mutation Research 324:69–76.

Kanbashi et al. (1997) "Frameshifts, base substitutions and minute deletions constitute X–ray–induced mutations in the endogenous tonB gene of *Escherichia coli* K12," Mutation Research 385:259–267.
Woychik et al. (1998) "Functional genomics in the post–genome era," Mutation Research 400:3–14.
Hera et al. (1996) "Use of an infectious Simian virus 40–based shuttle vector to analyze UV–induced mutagenesis in monkey cells," Mutation Research 364:235–243.
Guay–Woodford et al. (1996) "Evidence that two phenotypically distinct mouse PKD mutations, bpk and jcpk, are allelic," Kidney International 50:1158–1165.
Bultman et al. (1991) "Molecular characterization of a region of DNA associated with mutations at the agouti locus in the mouse," Proc. Natl. Acad. Sci. USA 88:8062–8066.
Woychik et al. (1990) "Molecular and genetic characterization of a radiation–induced structural rearrangement in mouse chromosome 2 causing mutations at the limb deformity and agouti loci," Proc. Natl. Acad. Sci. USA 87:2588–2592.
You et al. (1997) "Generation of radiation–induced deletion complexes in the mouse genome using embryonic stem cells," Methods: A Comparison to Methods in Enzymology 13:409–421.
Russell et al. (1979) "Specific–locus test shows ethylnitrosourea to be the most potent mutagen in the mouse," Proc. Natl. Acad. Sci. USA 76:5818–5819.
Hitotsumachi et al. (1985) "Dose–repetition increases the mutagenic effectiveness of N–ethyl–N–nitrosourea in mouse spermatogonia," Proc. Natl. Acad. Sci. USA 82:6619–6621.
Shedlovsky et al. (1993) "Mouse Models of Human Pheynlketonuia," Genetics 134:1205–1210.
Marker et al. (1997) "Spectrum of Bmp5 Mutations From Germline Mutagenesis Experiments in Mice," Genetics 145:435–443.
Zambrowicz et al. (1998) "Disruption and sequence identification of 2,000 genes in mouse embryonic stem cells," Nature 392:608–611.
Maniatis et al. (1987) "Regulation of Inducible and Tissue–Specific Gene Expression," Science 236:1237–1245.
Voss et al. (1986) "The role of enhancers in the regulation of cell–type–specific transcriptional control," Trends Biochem. Sci.11:287–289.

(List continued on next page.)

Primary Examiner—Joe Woitach
(74) Attorney, Agent, or Firm—Medlen & Carroll, LLP

(57) ABSTRACT

The present invention relates to methods of producing an allelic series of modifications in genes of interest in a cell. In particular, the invention provides methods for using nucleic acid sequence-modifying agents (e.g., chemicals, electromagnetic radiation, etc.) to introduce modifications in any nucleic acid sequence in the genome of a cell. Also provided are sets of cells which contain at least one modification in any gene of interest. The methods and compositions of the invention are useful in determining the function of the gene of interest.

7 Claims, No Drawings

OTHER PUBLICATIONS

Dijkema et al. (1985) "Cloning and expression of the chromosomal immune interferon gene of the rat," EMBO J. 4:761–767.

Uetsuki et al. (1989) "Isolation and Characterization of the Human Chromosomal Gene for Polypeptide Chain Elongation Factor–1α *,"J. Biol. Chem. 264:5791–5798.

Kim et al. (1990) "Use of the human elongation factor 1α promoter as a versatile and efficient expression system," Gene 91:217–223.

Mizushima and Nagata (1990) "pEF–BOS, a powerful mammalian expression vector," Nuc. Acids. Res. 18:5322.

Gorman et al. (1982) "The Rous sarcoma virus long terminal repeat is a strong promoter when introduced into a variety of eukaryotic cells by DNA–mediated transfection," Proc. Natl. Acad. Sci. USA 79:6777–6781.

Boshart et al. (1985) "A Very Strong Enhancer is Located Upstream of an Immediate Early Gene Human Cytomegalovirus," Cell 41:521–530.

Kohler et al. (1993) "Spectrum of Mutation and Frequency of Allelic Deletion of the p53 Gene in Ovarian Cancer," J. Natl. Cancer Inst. 85(18):1513–1519.

Greenman et al. (1998) "Identification of Missense and Truncating Mutations in the BRCA1 Gene in Sporadic and Familial Breast and Ovarian Cancer," Genes, Chromosomes & Cancer 21(3):244–249.

Zielenski and Tsui (1995) "Cystic Fibrosis: Genotypic and Phenotypic Variations," Ann. Rev. Genetics 29:777–807.

Dean and Santis (1994) "Heterogeneity in the severity of cystic fibrosis and the role of CFTR gene mutations," Hum. Genet. 93(4):364–368.

Sessa et al. (1997) "Autosomal dominant polycystic kidney disease: clinical and genetic aspects," J. Nephrol. 10(6):295–310.

Watnick et al. (1997) "An unusual pattern of mutation in the duplicated portion of PKD1 is revealed by use of a novel strategy for mutation detection," Human Molec. Genetics 6:1473–1481.

Veldhuisen et al. (1997) "A Spectrum of Mutations in the Second Gene for Autosomal Dominant Polycystic Kidney Disease (PKD2)," Am. J. Hum. Genet. 61:547–555.

Schulte–Merker et al. (1992) "The protein product of the zebrafish homologue of the mouse T gene is expressed in nuclei of the germ ring and the notochord of the early embryo," Development 116:1021–1032.

Hermann et al. (1990) "Cloning of the T gene required in mesoderm formation in the mouse," Nature 343:617–622.

Smith et al. (1990) "Expression of a Xenopus Homolog of Brachyury (T) Is an Immediate–Early Response to Mesoderm Induction," Cell 67:79–87.

Blum et al. (1992) "Gastrulation in the Mouse: The Role of the Homeobox Gene goosecoid," Cell 69:1097–1106.

Izpisua–Belmonte et al. (1993) "The Homeobox Gene goosecoid and the Origin of Organizer Cells in the Early Chick Blastoderm," Cell 76:645–659.

Blumberg et al. (1991) "Organizer–Specific Homeobox Genes in *Xenopus laevis* Embryos," Science 253:194–196.

Stachel et al. (1993) "Lithium perturbation and goosecoid expression identify a dorsal specification pathway in the pregastrula zebrafish," Development 117:1261–1274.

Evans et al. (1981) "Establishment in culture of pluripotential cells from mouse embryos," Nature 292:154–156.

Martin (1981) "Isolation of a pluripotent cell line from early mouse embryos cultured in medium conditioned by teratocarcinoma stem cells," Proc. Natl. Acad Sci. USA 78:7634–7638.

Magnuson et al. (1982) "The development of monosomy 19 mouse embryos," J. Embryo. Exp. Morph. 69:223–236.

Doetschman et al. (1988) "Establishment of Hamster Blastocyst Derived Embryonic Stem (ES) Cells," Dev. Biol. 127:224–227.

Tokunaga et al. (1989) "Establishment of the Mouse Embryonic Stem Cell Lines from Whole Blastocysts and Isolated Inner Cell Masses," Jpn. J. Anim. Reprod. 35:173–178.

Eistetter (1989) "Pluipotent Embryonal Stem Cell Lines Can Be Established from Disaggregated Mouse Morulae," Dev. Gro. Differ. 31:275–282.

Matsui et al. (1992) "Derivation of Pluripotential Embryonic Stem Cells from Murine Primordial Germ Cells in Culture," Cell 70:841–847.

Resnick et al. (1992) "Long–term proliferation of mouse primordial germ cells in culture," Nature 359:550–551.

Doetschman et al. (1985) "The in vitro development of blastocyst–derived embryonic stem cell lines: formation of visceral yolk sac, blood islands and myocardium," J. Embryol. Exp. Morphol. 87:27–45.

Lallemand et al. (1990) "An in situ assessment of the routes and extents of colonisation of the mouse embryo by embryonic stem cells and their descendants," Development 110:1241–1248.

Bradley et al. (1984) "Formation of germ–line chimaeras from embryo–derived teratocarcinoma cell lines," Nature 309:255–256.

Gossler et al. (1986) "Transgenesis by means of blastocyst–derived embryonic stem cell lines," Proc. Natl. Acad. Sci. USA 83:9065–9069.

Robertson et al. (1986) "Germ–line transmission of genes introduced into cultured pluripotential cells by retroviral vector," Nature 323:445–448.

Beddington et al. (1989) "An assessment of the developmental potential of embryonic stem cells in the midgestation mouse embryo," Development 105:733–737.

Suemori et al. (1990) "A mouse embryonic stem cell line showing pluripotency of differentiation in early embryos and ubiquitous β–galactosidase expression," Cell Differ. Dev. 29:181–186.

Strojek et al. (1990) "A Method for Cultivating Morphologically Undifferentiated Embryonic Stem Cells from Porcine Blastocysts," Theriogenology 33:901–914.

Piedrahita et al. (1990) "On the Isolation of Embryonic Stem Cells: Comparative Behavior of Murine, Porcine and Ovine Embros," Theriogenology 34:879–901.

Notarianni et al. (1991) "Derivation of pluripotent, embryonic cell lines from the pig and sheep," J. Reprod. Fert. (Suppl.) 43:255–260.

Saito et al. (1992) "Bovine embryonic stem cell–like cell lines cultured over several passages," Roux's Arch. Dev. Biol. 201:134–141.

Stice et al. (1996) "Pluripotent Bovine Embryonic Cell Lines Direct Embryonic Development Following Nuclear Transfer," Biol. Reprod. 54:100–110.

Sukoyan et al. (1992) Isolation and Cultivation of Blastocyst–Derived Stem Cell Lines from American Mink (*Mustela vison*) Mol. Reprod. Dev. 33:418–431.

Brenin et al. (1997) "Rat Embryonic Stem Cells: A Progress Report" Transplant Proc. 29:1761–1765.

Iannaccone et al. (1994) "Pluripotent Embryonic Stem Cells from the Rat Are Capable of Producing Chimeras," Dev. Biol. 163:288–292.

Sun et al. (1995) "ES–like cell cultures derived from early zebrafish embryos," Mol. Mar. Biol. Biotechnol. 4:193–199.

Evans (1989) "Potential for Genetic Manipulation of Mammals," Mol. Bio. Med. 6:557–565.

Johnson et al. (1989) "Genetic Correction of Hereditary Disease," Fetal Ther. 4 (Suppl.) 1:28–39.

Babinet et al. (1989) "Transgenic Mice," Genome 31:938–949.

Russell et al. (1990) "Factors affecting the nature of induced mutations," in *Biology of Mammalian germ Mutagenesis*, Banbury Report 34, Cold Spring Harbor Laboratory Press, pp. 271–289.

Rinchik (1991) "Chemical mutagenesis and fine–structure functional analysis of the mouse genome," Trends in Genetics 7(1):15–21.

Sehlmeyer and Wobus (1994) "Lower mutation frequencies are induced by ENU in undifferentiated embryonic cells than in differentiated cells of the mouse in vitro," Mutation Research 324:69–76.

Shibuya and Morimoto (1993) "A review of the genotoxicity of 1–ethyl–1–nitrosourea," Mutation Res. 297:3–38.

Justice et al. (1988) "Three ENU–induced alleles of the murine quaking locus are recessive embryonic lethal mutations," Genet. Res. 51:95–102.

Vitaterna et al. (1994) "Mutagenesis and Mapping of a Mouse Gene, Clock, Essential for Circadian Behavior," Science 264:719–725.

Hammer et al. (1986) "Genetic Engineering of Mammalian Embryos," J. Animal Sci:63:269–278.

Hammer et al. (1985) "Production of transgenic rabbits, sheep and pigs by microinjection," Nature 315:680–683.

Bradley et al. (1987) in *Teratocarcinomas and Embryonic Stem Cells: A Practical Approach*, Ed. Robertson E.J. (IRL, Oxford, U.K.), pp. 113–151.

Nagy et al. (1990) "Embryonic stem cells alone are able to support fetal development in the mouse," Development 110:815–821.

Miki et al. (1994) "A Strong Candidate for the Breast and Ovarian Cancer Susceptibility Gene BRCA1," Science 266:66–71.

Friedman et al. (1994) "Confirmation of BRCA1 by analysis of germline mutations linked to breast and ovarian cancer in ten families," Nat. Genet. 8:399–404.

\* cited by examiner

ALLELIC SERIES OF GENOMIC MODIFICATIONS IN CELLS

FIELD OF THE INVENTION

The present invention relates to methods of producing modifications in genes of interest in a cell. In particular, the invention provides methods for using nucleic acid sequence-modifying agents to introduce modifications in any gene of interest in the genome of a cell. Also provided are sets of cells which contain at least one modification in any gene of interest. The methods and compositions of the invention are useful in determining the function of the gene of interest.

BACKGROUND OF THE INVENTION

With the completion of the Human Genome Program approaching, there is an increasing interest in studying the function of genes, particularly those involved in human development and disease. While mapping and nucleotide sequencing of genes is an important first step for understanding the function of genes, the physical characterization of the structure of a gene does not provide insight into the function of that gene in the context of a multicellular organism.

For example, prior art approaches to determining gene function in mammals have relied on targeting mutations to specific genes in embryonic stem (ES) cells, or on genome-wide mutagenesis techniques designed to mutate all genes of an organism (e.g., mice). For example, "knock-out" mutations in ES cells have been widely used to target mutations to specific genes. "Knock-out" mutations shut off or alter gene expression and are currently used to produce a phenotype in the whole animal which reflects the function of the knocked-out gene. This approach has identified many genes which are associated with cancer and other human genetic diseases, and relies either on phenotype-based screens (i.e., screening for a particular phenotype) or on gene-based screens (i.e., screening for a particular alteration in the genome). Phenotype-based screens have primarily been conducted using mice, and involve characterization of thousands of mutagenized mice for specific diseases and traits [Russell et al., Proc. Natl. Acad. Sci. USA 76:5818–5819, 1979; Hitotsumachi et al., Proc. Natl. Acad. Sci. USA 82:6619–6621; Shedlovsky et al., Genetics 134:1205–1210; Marker et al., Genetics 145:435–443, 1997]. While the phenotype-based approach has the advantage that no assumption is made with respect to which genes are associated with a given disease or disorder, it is nevertheless very costly when using organisms such as mice since it requires the maintenance of several lines of mutagenized whole organisms. Furthermore, it is unclear whether phenotype-based screens permit conducting saturation screens for both dominant and recessive mutations of all mouse genes.

Gene-based screens have been carried out in whole animals and in embryonic stem (ES) cells. This approach involves identifying the organism's genes or the ES cell genes which have been mutated. Homologous recombination and retroviral insertion are commonly used in ES cells [Zambrowicz et al. (1998) Nature 392:608–611]. Although mutagenesis by homologous recombination is becoming routine, it remains cumbersome and expensive. Similarly, while the genome-wide approach to mutagenizing ES cells by retroviral insertional mutagenesis allows the generation of a large number of mutagenized ES cells in a cost effective manner, this approach produces only one, or a limited number of, alleles of a given gene. Additionally, the class of mutations that can be produced with this approach is limited to those mutations which result from integration of a retroviral element. Thus, mutations caused by, for example, single amino acid changes in the protein cannot be produced using this approach. In many instances, for example, it may be desirable to generate mutations which cause single amino acid changes that merely modify gene function (e.g., by generating hypomorphic alleles that express the gene with a reduced efficiency) or that give rise to a new trait in the animal (e.g., by generating dominant neomorphic alleles which result in a gain of function). The generation of hypomorphic and neomorphic alleles of a gene in a model organism by single amino acid substitutions may be desirable to create a model organism for a human trait or disease in which gene function is modified rather than destroyed.

Accordingly, what is needed are methods for determining gene function which may efficiently be applied on a genome-wide scale, which generate more than one mutation in a gene of interest, and which do not only abrogate the function of the gene.

SUMMARY OF THE INVENTION

The invention provides methods for generating an allelic series of modifications in any gene of interest contained in a cell using nucleic acid sequence-modifying agents. In particular, the invention provides a method of producing a modification in a gene of interest contained in a cell, comprising: a) providing: i) a plurality of target cells capable of being cultured; ii) an agent capable of producing at least one modification in the gene of interest in the target cell; b) treating the target cells with the agent under conditions such that a mixture of cells is produced, the mixture of cells comprising cells having an unmodified gene of interest and cells having a is modified gene of interest; and c) isolating the cells having a modified gene of interest.

In one preferred embodiment, the methods of the invention further comprise step d) comparing the nucleotide sequence of the gene of interest in the cells having a modified gene of interest with the nucleotide sequence of the gene of interest in the cells having an unmodified gene of interest. In a more preferred embodiment, the methods further comprise e) manipulating the cells having a modified gene of interest to generate an organism comprising the modification in the gene of interest. In an alternative more preferred embodiment, the method further comprises prior to step d) amplifying the modified gene of interest to produce an amplified modified gene of interest. In yet a more preferred embodiment, the method further comprises prior to step d) sequencing the amplified modified gene of interest.

Without intending to limit the methods of the invention to any particular modification, in one embodiment, the modification is selected from the group consisting of mutation, mismatch, and strand break. In a preferred embodiment, the mutation is selected from the group consisting of deletion, insertion and substitution. In another preferred embodiment, the strand break is selected from the group consisting of single-strand break and double-strand break. While it is not intended that the scope of the invention be limited to any particular type or source of target cell, in one embodiment, the target cell is derived from an organism selected from the group consisting of non-human animal, plant, protist, fungus, bacterium, and virus. In a preferred embodiment, the non-human animal is a mammal. In a more preferred embodiment, the mammal is a mouse. In an alternative preferred embodiment the non-human animal is zebrafish. In another embodiment, the target cell is an embryonic stem cell.

The invention is not intended to be limited to any particular type or class of agent capable of producing at least one modification in the gene of interest. However, in one preferred embodiment, the agent is selected from the group consisting of N-ethyl-N-nitrosurea, methylnitrosourea, procarbazine hydrochloride, triethylene melamine, acrylamide monomer, chlorambucil, melphalan, cyclophosphamide, diethyl sulfate, ethyl methane sulfonate, methyl methane sulfonate, 6-mercaptopurine, mitomycin-C, procarbazine, N-methyl-N'-nitro-N-nitrosoguanidine, $^3H_2O$, urethane, ultraviolet light, X-ray radiation, and gamma-radiation. The invention further provides a method of producing an allelic series of modification in a gene of interest contained in a cell, comprising: a) providing: i) a plurality of target cells capable of being cultured; ii) an agent capable of producing at least one modification in the gene of interest in the target cell; b) treating the target cells with the agent under conditions such that a mixture of cells is produced, the mixture of cells comprising cells having an unmodified gene of interest, cells having a first modification in the gene of interest, and cells having a second modification in the gene of interest; and c) isolating the cells having a first modification in the gene of interest and the cells having a second modification in the gene of interest, thereby producing an allelic series of modification in the gene of interest. In one preferred embodiment, the method further comprises step d) comparing the nucleotide sequence of the gene of interest in the cells having an unmodified gene of interest with the nucleotide sequence of the gene of interest in cells selected from the group consisting of the cells having a first modification in the gene of interest and the cells having a second modification in the gene of interest. In a more preferred embodiment, the method further comprises e) manipulating cells selected from the group consisting of the cells having a first modification in the gene of interest and the cells having a second modification in the gene of interest to generate an organism comprising a modification selected from the group consisting of the first modification in the gene of interest and the second modification in the gene of interest. In an alternative more preferred embodiment, the method further comprises prior to step d) amplifying the gene of interest selected from the group consisting of the gene of interest having the first modification and the gene of interest having the second modification too produce amplified modified gene of interest selected from the group consisting of amplified gene of interest having the first modification and amplified gene of interest having the second modification. In yet a more preferred embodiment, the method further comprises prior to step d) sequencing the amplified modified gene of interest.

Without limiting the invention to any particular class or type of modification, in an alternative preferred embodiment, the first modification and the second modification are selected from the group consisting of mutation, mismatch, and strand break. In a more preferred embodiment, the mutation is selected from the group consisting of deletion, insertion and substitution. In an alternative preferred embodiment, the strand break is selected from the group consisting of single-strand break and double-strand break. The invention is not limited to any particular type or source of target cell.

However, in one preferred embodiment, the target cell is derived from an organism selected from the group consisting of non-human animal, plant, protist, fungus, bacterium, and virus. In a more preferred embodiment, the non-human animal is a mammal. In yet a more preferred embodiment, the mammal is a mouse. In an alternative preferred embodiment, the non-human animal is zebrafish. In another preferred embodiment, the target cell is an embryonic stem cell. Without intending to limit the methods of the invention to any particular class or type of agent capable of producing at least one modification in the gene of interest, in one preferred embodiment, the agent is selected from the group consisting of N-ethyl-N-nitrosurea, methylnitrosourea, procarbazine hydrochloride, triethylene melamine, acrylamide monomer, chlorambucil, melphalan, cyclophosphamide, diethyl sulfate, ethyl methane sulfonate, methyl methane sulfonate, 6-mercaptopurine, mitomycin-C, procarbazine, N-methyl-N'-nitro-N-nitrosoguanidine, $^3H_2O$, urethane, ultraviolet light, X-ray radiation, and gamma-radiation.

The invention further provides a method of producing a modification in a gene of interest contained in a cell, comprising: a)-providing: i) a plurality of target cells capable of being cultured; ii) an agent capable of producing at least one modification in the gene of interest in the target cell; b) treating the target cells with the agent under conditions such that a mixture of cells is produced, the mixture of cells comprising a cell having an unmodified gene of interest and two or more cells having a modified gene of interest, the two or more cells having different modifications in the gene of interest; and c) isolating the two or more cells having a modified gene of interest.

In one embodiment, the method further comprises step d) comparing the nucleotide sequence of the gene of interest in the cells having a modified gene of interest with the nucleotide sequence of the gene of interest in the cells having an unmodified gene of interest. In a more preferred embodiment, the method further comprises e) manipulating the cells having a modified gene of interest to generate an organism comprising the modification in the gene of interest. In an alternative preferred embodiment, the method further comprises prior to step d) amplifying the modified gene of interest to produce an amplified modified gene of interest. In yet a more preferred embodiment, the method further comprises prior to step d) sequencing the amplified modified gene of interest.

While not intending to limit the invention to any particular type of modification, in one embodiment, the modification is selected from the group consisting of mutation, mismatch, and strand break. In a preferred embodiment, the mutation is selected from the group consisting of deletion, insertion and substitution. In an alternative preferred embodiment, the strand break is selected from the group consisting of single-strand break and double-strand break.

The invention is not limited to any particular type or source of target cell. However, in one embodiment, the target cell is derived from an organism selected from the group consisting of non-human animal, plant, protist, fungus, bacterium, and virus. In a preferred embodiment, the non-human animal is a mammal. In a more preferred embodiment, the mammal is a mouse. In an alternative preferred embodiment, the non-human animal is zebrafish. In another embodiment, target cell is an embryonic stem cell.

It is not intended that the invention be limited to the type or class of agent capable of producing at least one modification in the gene of interest. However, in one embodiment, the agent is selected from the group consisting of N-ethyl-N-nitrosurea, methylnitrosourea, procarbazine hydrochloride, triethylene melamine, acrylamide monomer, chlorambucil, melphalan, cyclophosphamide, diethyl sulfate, ethyl methane sulfonate, methyl methane sulfonate, 6-mercaptopurine, mitomycin-C, procarbazine, N-methyl- N'-nitro-N-nitrosoguanidine, $^3H_2O$, urethane, ultraviolet light, X-ray radiation, and gamma-radiation.

Definitions

To facilitate understanding of the invention, a number of terms are defined below.

The term "genomic sequence" refers to any deoxyribonucleic acid sequence located in a cell. Genomic sequences include, but are not limited to, structural genes, regulatory genes, and regulatory elements.

A "transgenic organism" as used herein refers to an organism whose germ line cells have been altered by the introduction of a transgene. The term "transgene" as used herein refers to any nucleic acid sequence which is introduced into the genome of an organism by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The terms "heterologous DNA sequence" and "foreign DNA sequence" are used interchangeably herein to refer to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification relative to the endogenous DNA sequence. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

As used herein, the term "gene" means the deoxyribonucleotide sequences comprising the coding region of a structural gene and including sequences located adjacent to the coding region on both the 5' and 3' ends for a distance of several KB on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. A genomic form or clone of a gene contains coding sequences, termed exons, alternating with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein the term "coding region" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, enhancer elements, etc. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., Science 236:1237 (1987)]. For example, the SV40 early gene enhancer is very active in a wide variety of cell types from many mammalian species and has been widely used for the expression of proteins in mammalian cells [Dijkema, et al., EMBO J. 4:761 (1985)]. Other examples of promoter/enhancer elements active in a broad range of mammalian cell types are those from the human elongation factor 1α gene-[Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart el al, Cell 41:521 (1985)].

The terms "gene of interest" and "nucleotide sequence of interest" refer to any gene or nucleotide sequence, respectively, the manipulation of which may be deemed desirable for any reason by one of ordinary skill in the art.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are mutations, mismatches, strand breaks, as well as covalent and non-covalent interactions between a nucleic acid sequence (which contains unmodified and/or modified nucleic acids) and other molecules. Illustrative of a covalent interaction between a nucleic acid sequence and another molecule are changes to a nucleotide base (e.g., formation of thymine glycol) and covalent cross-links between double-stranded DNA sequences which are introduced by, for example, ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribnucleic acid sequence. The present invention contemplates modifications which cause changes in a functional property (or properties), such changes manifesting themselves at a variety of time points.

The term "allelic series" when made in reference to a gene refers to wild-type sequences of the gene. An "allelic series of modifications" as used herein in reference to a gene refers to two or more nucleic acid sequences of the gene, where each of the two or more nucleic acid sequences of the gene contains at least one modification when compared to the wild-type sequences of the gene.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch is present.

The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence. Strand breaks may be introduced into a double stranded nucleic acid sequence either directly (e.g., by ionizing radiation) or indirectly (e.g., by enzymatic incision at a nucleic acid base).

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

The term "modified cell" refers to a cell which contains at least one modification in the cell's genomic sequence.

The term "nucleic acid sequence-modifying agent" refers to an agent which is capable of introducing at least one modification into a nucleic acid sequence. Nucleic acid sequence-modifying agents include, but are not limited to, chemical compounds [e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6 MP), mitomycin-C (MMC), procarbazine (PRC), N-methyl-N'-nitro-N-nitrosoguanidine (MNNG), $^3H_2O$, and urethane (UR)], and electromagnetic radiation [e.g., X-ray radiation, gamma-radiation, ultraviolet light].

The term "wild-type" when made in reference to a gene refers to a gene which has the characteristics of that gene when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

DESCRIPTION OF THE INVENTION

The invention provides methods for efficiently generating an allelic series of modifications in any gene of interest contained in a cell using nucleic acid sequence-modifying agents. The methods of the invention contemplate generation of an allelic series of modifications in more than one gene in the genome of a target cell, and preferably in substantially every gene within the genome of the target cell. The allelic series of modifications in any gene of interest may be analyzed in the manner described herein. The methods of the invention also provide a set of cells which contain one or more modifications in substantially every gene within the genome of the cells (i.e., the "Library"). These methods allow screening the Library for modifications in a gene of interest prior to further using cells from the Library for determining the function of the gene of interest. The methods provided herein are particularly useful in modifying genes of interest in mammalian ES cells.

The methods of the invention involve treating a population of cells with one or more agents (e.g., nucleic acid sequence-modifying agents) which are capable of introducing one or more modifications in substantially every gene within the geneline of the cells. The term "substantially every gene" refers to the statistical probability, preferably at least about 70% probability, more preferably at least about 85% probability, and most preferably at least about 95% probability, as determined by a standard Poisson distribution, that each gene in the genome contains at least one modification. The resulting mutant cells which contain the genomic modifications are clonally expanded (e.g., into 500,000 clones) to produce a library of clones, each clone containing at least one modification in at least one gene of interest. Each clone is expanded and screened in order to determine the DNA sequence of the modified gene of interest as well as to determine the type and location of the modification in the gene of interest. DNA sequencing may be performed by sequence analysis (preferably using automated sample processing with robotics technologies and molecular analysis using DNA chip technologies), or high throughput methods (e.g., single stranded conformational polymorphism (SSCP), chemical cleavage, and heteroduplex analysis). The nucleic acid sequences which are obtained for the one or more genes of interest from each clone provide a database by which each clone is uniquely identified. Thus, modified cells may be selected from the Library based on cross reference to the nucleic acid sequence data.

Selected modified cells (i.e., cells containing one or more modifications in the gene of interest) may further be used to determine the function of the gene of interest.

This may be accomplished by, for example, culturing the selected modified cells and determining changes in the modified cells' morphological, biochemical, and molecular biological characteristics as compared to those characteristics in wild-type cells (i.e., cells which had not been treated with the nucleic acid sequence-modifying agent). Alternatively, where the selected modified cells are capable of regenerating a multicellular organism (e.g., ES cells), these cells may be used to generate transgenic non-human organisms which are further investigated to determine morphological, biochemical, behavioral, histological, and molecular biological changes relative to control non-human organisms, i.e., non-human organisms which are generated from progenitor cells that had not been exposed to the nucleic nucleic acid sequence-modifying agent.

The modified cells which collectively harbor an allelic series of modifications in substantially every gene are particularly useful in investigating diseases which are associated with more than one modification in a given gene. Several such diseases are known in the art including, for example, epithelial ovarian cancer, sporadic breast cancer, familial breast cancer, cystic fibrosis, and autosomal dominant polycystic kidney disease. For example, epithelial ovarian cancer has been associated with 45 mutations in exons 5–8 of the p53 gene. Overall, 72% of the mutations were transitions, 24% were transversions, and 4% were microdeletions. Allelic deletion of the other p53 allele was seen in 67% of ovarian cancers in which a p53 mutation was present [Kohler et al. (1993) J. Natl. Cancer Inst. 85(18): 1513–1519]. Similarly, familial breast cancer has also been shown to be associated with over 200 distinct mutations in the BRCA1 gene, including missense and protein-truncating mutations [Greenman et al. (1998).21(3):244–249]. Cystic fibrosis was found to be associated with over 550 mutations in the cystic fibrosis transmembrane conductance regulator (CFTR) gene [see, e.g., [Zielenski and Tsui (1995) Ann. Rev. Genetics 29:777–807; Dean and Santis (1994) Hum. Genet. 93(4):364–368]. A list of the mutations associated with cystic fibrosis is available at www.genet.sickkids.on.ca/cftr. Another disease associated with several mutations in a given gene is autosomal dominant polycystic kidney disease (ADPKD) in which phenotypically indistinguishable traits are caused by mutations in at least three distinct autosomal genes, i.e., PKD1, PKD2 and PKD3 [Sessa et al. (1997) J. Nephrol. 10(6):295–310; Watnick et al. (1997) Hum. Molec. Genetics 6:1473–1481; Veldhuisen et al. (1997) 61:547–555].

The modified cells which collectively harbor an allelic series of modifications in substantially every gene are particularly useful in investigating diseases which are associated with more than one modification in a given gene. Several such diseases are known in the art including, for example, epithelial ovarian cancer, sporadic breast cancer, familial breast cancer, cystic fibrosis, and autosomal dominant polycystic kidney disease. For example, epithelial ovarian cancer has been associated with 45 mutations in exons 5–8 of the p53 gene. Overall, 72% of the mutations were transitions, 24% were transversions, and 4% were microdeletions. Allelic deletion of the other p53 allele was seen in 67% of ovarian cancers in which a p53 mutation was present [Kohler et al. (1993) J. Natl. Cancer Inst. 85(18): 1513–1519]. Similarly, familial breast cancer has also been shown to be associated with over 200 distinct mutations in the BRCA1 gene, including missense and protein-truncating mutations [Greenman et al. (1998) 21(3):244–249]. Cystic fibrosis was found to be associated with over 550 mutations in the cystic fibrosis transmembrane conductance regulator (CFTR) gene [see, e.g., [Zielenski and Tsui (1995) Ann. Rev. Genetics 29:777–807; Dean and Santis (1994) Hum. Genet. 93(4):364–368]. A list of the mutations associated with cystic fibrosis is available at http://www.genet.sickkids.on.ca/cftr. Another disease associated with several mutations in a given gene is autosomal dominant polycystic kidney disease (ADPKD) in which phenotypically indistinguishable traits are caused by mutations in at least three distinct autosomal genes, i.e., PKD1, PKD2 and PKD3 [Sessa et al. (1997) J. Nephrol. 10(6):295–310; Watnick et al. (1997) Hum. Molec. Genetics 6:1473–1481; Veldhuisen et al. (1997) 61:547–555].

The methods of the invention provide several advantages over prior art methods for determining gene function. For example, unlike the prior art's retroviral insertional mutagenesis approach [Zambrowicz et al. (1998) Nature 392:608–611], the methods provided herein are not limited to the identification of genes into which a retroviral sequence is capable of inserting. Instead, the methods provided herein exploit an approach in which different types of modifications of a gene of interest are randomly introduced into any part of that gene. In particular, prior art methods which rely on insertion of a retroviral sequence into a gene suffer from the drawback that they result in only one class of mutations, i.e., insertions. Since many human diseases (e.g., cystic fibrosis and epithelial ovarian cancer) involve modifications other than only insertions in a gene (e.g., single nucleotide changes such as transitions, transversions, and deletions), prior art approaches which rely on retroviral insertional mutagenesis fail to generate major classes of mutations which are relevant to human diseases. Moreover, the methods provided herein permit evaluation of the function of a gene of interest in a more rapid and more cost effective manner than prior art methods which rely on investigating gene function through mutagenesis in whole animals. This is because the methods of the invention allow a preliminary screening of treated cultured cells for genomic modifications, and selecting only those clones which contain modifications in the gene of interest. Since screening and selection are performed using treated cultured cells rather than whole animals, thousands of treated cultured cells may rapidly be analyzed for genomic modifications using automated sample processing with robotics technologies and molecular analysis using DNA chip technologies. Furthermore, since treated cells-may be recovered-following cryopreservation, the cost of maintaining a cell line containing a modification in a gene of interest is substantially less than the cost of maintaining a line of transgenic animals in which the gene of interest is modified.

Additionally, unlike the phenotype-based screens of the prior art, the methods provided herein are not limited to only the identification of genes whose function is associated with expression of a phenotype in the non-human organism which is generated from the modified cell. Rather, because the methods of the invention preferably employ nucleic acid sequence-based screens instead of only phenotype-based screens, the methods provided herein allow selection of modified cells in which the modified gene of interest contains a modification which produces amorphic (recessive null) alleles, hypomorphic recessive alleles that express the gene with a reduced efficiency, hypermorphic recessive alleles that express the gene with greater than wild-type activity, as well as antimorphic (dominant negative) and neomorphic (gain of function) alleles.

The invention is further described under (1) Construction Of An Allelic Series Of Modifications In A Library Of Cell Clones Containing Genomic Modifications Using Nucleic Acid Sequence-Modifying Agents, (2) Accessing Clones In the Library, and (3) Determining Gene Function.

1. Construction Of An Allelic Series Of Modifications In A Library Of Cell Clones Containing Genomic Modifications Using Nucleic Acid Sequence-Modifying Agents The methods of the invention are contemplated to involve treating cultured cells form any organism with one or more agents which are capable of introducing at least one modification into genomic sequences including, but not limited to, structural genes, regulatory genes, and regulatory elements. Treatment with the nucleic acid sequence-modifying agent is contemplated to produce the Library, i.e., a set of cells which collectively contain one or more modifications in substantially every gene within the genome of the cells. The methods of the invention are herein illustrated by, but not limited to, treatment of mouse embryonic stem cells with N-ethyl-N-nitrosurea 1 N-methyl-N'-nitro-N-nitrosoguanidine, or methyl methane sulfonate.

A. Organisms

The methods of the invention are not intended to be limited to the type of organism from which the cells to be treated with the nucleic acid sequence-modifying 2V agent are derived. Rather, any organism in which the function of a genomic sequence to is sought to be determined is contemplated to be within the scope of the invention. Such organisms include, but are not restricted to, non-human animals (e.g., vertebrates, invertebrates, mammals, fish, insects, etc.), plants (e.g., monocotyledon, dicotyledon, vascular, non-vascular, seedless, seed plants, etc.), protists (e.g., algae, citliates, diatoms, etc.), fungi (including multicellular forms and the single-celled yeasts), bacteria (prokaryotic, eukaryotic, archaebacteria, etc.), and viruses. In a preferred embodiment the organism is a non-human animal. A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

In yet a more preferred embodiment, the non-human animal is a mouse. The mouse offers several advantages with respect to modeling human disease. For example, most genes in humans have functional homologues in the mouse. In addition, because the anatomy and physiology of the mouse are similar to those of humans, the phenotype of genetic diseases are very similar in the two organisms. Importantly, the mouse's small size, high reproductive capacity, extensive history of classical and molecular genetic analyses, and ease of genetic manipulation make it a preferred organism for studying the roles of genes in human disease.

In an alternative preferred embodiment, the non-human animal is a zebrafish. Zebradfish are a preferred model for the determination of DNA function in mammals for several reasons. First, zebrafish is a complex vertebrate species which contains a majority of those genes found in higher vertebrates such as man. Moreover, nucleotide sequences are highly conserved between analogous zebrafish and mammalian genes [Schulte-Merker et al (1992) *Development* 116:1021–1032; Hermann et al (1990) *Nature* 343:617–622; Smith et al(1990) *Cell* 67:79–87; Blum et al (1992) Cell 69:1097–1106; Izpisua-Belmonte et al (1993) *Cell* 76:645–659; Blumberg et al (1991) *Science* 253:194–196; Stachel et al (1993) *Development* 117:1261–1274].

B. Cells

Any type of cell capable of being cultured is expressly included within the scope of this invention. The term "cell capable of being cultured" as used herein refers to a cell which is able to divide in vitro to produce two or more progeny cells. 2' Such cells are exemplified by embryonic cells (e.g., embryonic stem cells, fertilized egg cells, 2-cell embryos, protocorm-like body cells, callus cells, etc.), adult cells (e.g., brain cells, fruit cells, etc.), undifferentiated cells (e.g., fetal cells, tumor cells, etc.), differentiated cells (e.g., skin cells, liver cell, etc.), and the like.

In a preferred embodiment, the cell is capable of regenerating a multicellular organism. The use of such cells for the determination of gene function is preferred since multicellular organisms provide a living in vivo system in which the effects of modifying a gene of interest much more closely resemble those in a living organism as compared to in vitro cultured cells. In a more preferred embodiment, the cells are capable of contributing to the germline of the regenerated multicellular organism.

In a particularly preferred embodiment, the cell which is treated with the nucleic acid sequence-modifying agent and which is used to regenerate a multicellular organism is an embryonic stem (ES) cell. ES cells are pluripotent cells directly derived from the inner cell mass of blastocysts [Evans et al., (1981) Nature 292:154–156; Martin (1981) Proc. Natl. Acad. Sci. USA 78:7634–7638; Magnuson et al., (1982) J. Embryo. Exp. Morph. 81:211–217; Doetchman et al., (1980) Dev. Biol. 127:224–227], from inner cell masses [Tokunaga et al., (1989) Jpn. J. Anim. Reprod. 35:113–178], from disaggregated morulae [Eistetter, (1989) Dev. Gro. Differ. 31:275–282] or from primordial germ cells [Matsui et al., (1992) Cell 70:841–847; Resnick et al., (1992) Nature 359:550–551]. These cells give rise to the endodermal, ectodermal, and mesodermal compartments [Doetschman et al. (1985) J. Embryol. Exp. Morphol. 87:27].

Embryonic stem cells are preferred for determining the function of a gene since they offer a number of advantages. For example, ES cells are capable of forming permanent cell lines in vitro, thus providing an unlimited source of genetic material. Importantly, because the genetic material of ES cells may be introduced into the germline of a regenerated multicellular organism, ES cell genes which are modified by the methods disclosed herein may be introduced into the germline of regenerated multicellular organisms thus offering the opportunity to determine the function of the genes in the organism.

In a particularly preferred embodiment, the ES cells are mouse ES cells. Mouse ES cells are available from the ATCC and can be cultured over at least sixty passages and typically retain a normal karyotype. Embryonic stem cells have been shown to remain in undifferentiated form in vitro if maintained on embryonic fibroblast feeder cell layers. In cell suspension, they will begin differentiation, containing elements of glandular, heart, skeletal smooth muscle, nerve, keratin-producing cells, and melanocytes [Doetschman (1988) et al. Dev. Biol. 127:224–227].

An additional advantage to using ES cells is that they are the most pluripotent cultured animal cells known. For example, when ES cells are injected into an intact blastocyst cavity or under the zona pellucida, at the morula stage embryo, ES cells are capable of contributing to all somatic tissues including the germ line in the resulting chimeras [reviewed by Bradley (1990) Curr. Op. Cell. Biol. 2:1013–1017; see also Lallemand et al. (1990) Development 110:1241–1248; Bradley et al. (1984) Nature 309:255–256; Gissker et al. (1986) Proc. Natl. Acad. Sci. USA 83:9065–9069; Robertson et al. (1986) Nature 323:4745–448]. Indeed, their ability to colonize the various embryonic tissues is not equal. They are able to extensively colonize fetal tissues and extraembryonic mesoderm, but may be restricted in their capability to contribute to trophectoderm and primitive endoderm derivatives [Beddington et al. (1989) Development 105:733–737; Suemori et al. (1990) Cell Differ. Dev. 29:181∝186].

Embryonic stem cell-like cells have been obtained from pig [Strojek et al. (1990) Theriogenology 33:901–914; Piedrahita et al. (1990) Theriogenology 34:879–901], sheep [Piedrahita et al. (1990) Theriogenology 34:879–901; Notarianni et al. (1991) J. Reprod. Fert. (Suppl.) 43:255–260], cattle [Saito et al (1992) Roux's Arch. Dev. Biol. 201:134–141; Stice et al. (1996) Biol. Reprod. 54:100–110; Talbot et al. (1995) 42:35–52], American mink [Sukoyan et al. (1992) Mol. Reprod. Dev. 33:418–431], rat [Brenin et al. (1997) Transplant Proc. 29:1761–1765; Iannaccone et al. (1994) Dev. Biol. 163:288–292], hamster [Doetschman et al. (1988) 127:224–227], and zebrafish [Sun et al. (1995) Mol. Mar. Biol. Biotechnol. 4:193–199]. In addition, the international application WO 90/03432 discloses pluripotential embryonic stem cell-like cells derived from porcine and bovine species. This international application describes the production of pluripotential ungulate embryonic stem cells, together with details of the morphology enabling recognition of the cells.

Yet a further advantage to using ES cells to determine gene function is that ES cells can be cultured and manipulated in vitro and then returned to the embryonic environment to contribute to all tissues including the germ line [for a review, see Robertson (1986) Trends in Genetics 2:9–13; Evans (1989) Mol. Bio. Med. 6:557–565; Johnson et al. (1989) Fetal Ther. 4 (Suppl.) 1:28–39; Babinet et al. (1989) Genome 31:938–949]. Not only can embryonic stem cells propagated in vitro contribute efficiently to the formation of chimeras, including germ line chimeras, but in addition, these cells can be manipulated in vitro without losing their capacity to generate germ line chimeras [Robertson et al. (1986) Nature 323:445–447].

C. Nucleic Acid Sequence-Modifying Agents

The methods of the invention are contemplated to include within their scope any agent which is capable of introducing a modification into the genome of a cell. These agents are exemplified by chemicals and electromagnetic radiation. Exemplary chemicals are described at dir.niehs.nih.gov/dirtb/dirrtg/chemicalsstudiedindex2.htm including, but not limited to, N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methanesulfonate (MMS), 6-mercaptopurine (6 MP), mitomycin-C (MMC), procarbazine (PRC), N-methyl-N'-nitro-N-nitrosoguanidine (MNNG), $^3H_2O$, and urethane (UR) [see, e.g., Russell et al., Factors affecting the nature of induced mutations, In "Biology of Mammalian Germ Cell Mutagenesis," Banbury Report 34, Cold Spring Harbor Laboratory Press (1990), pp. 271–289; Rinchik (1991) Trends in Genetics 7(1); Marker et al. (1997) Genetics 145:435–443]. Electromagnetic radiation is exemplified by ultraviolet light, X-ray radiation, gamma-radiation, etc.

In one preferred embodiment, the nucleic acid sequence-modifying agent is N-ethyl-N-nitrosurea (ENU). ENU is a preferred compound for generating an allelic series of modifications in a cell's genome because it can produce point mutations (and, less frequently, small deletions) at sites throughout a gene, and is at least 10-fold more efficient in generating mutations than other agents [Russell et al., Proc. Natl. Acad. Sci. USA 76, 5818–5819, 1979; Hitotsumachi et al., PNAS 82, 6619–6621; Shedlovsky et al., Genetics 134, 1205–1210; Marker et al., Genetics 145, 435–443, 1997]. In addition, ENU has been shown to be effective in inducing mutations in undifferentiated embryonal carcinoma (EC) cells [Schlmeyer and Wobus (1994) Mutation Res. 324:69–76], and in differentiated cell lines such as Chinese hamster ovary (CHO), V79, mouse S49, and GRSL13-2 cells, as well as human lymphoblasts and lymphocytes [Shibuya and Morimoto, Mutation Res. (1993) 197:3–38]. Moreover, ENU has also been shown to produce antimorphic (dominant negative) and neomorphic (gain of function) alleles [Justice et al. (1988) Genet. Res. 51:95–102; Vitatema et al. (1994) Science 264:719–725]. Furthermore, based on data provided herein, it is contemplated by the inventors that at least one point mutation may be introduced into every gene by treating as few as from about 200 to about 600 cells with ENU.

One of skill in the art appreciates that the frequency of modification with a given nucleic acid sequence-modifying agent may be manipulated by treating the target cells with different doses of the agent and/or at multiple times. One of skill in the art also appreciates that treating cells with nucleic acid sequence-modifying agents involves using a non-toxic concentration (i.e., a concentration which does not kill all the treated cells or which does not destroy the treated cells' ability to regenerate a multicellular organism). Such a concentration may empirically be determined and is within the ordinary skill in the art. For example, a 60-mm dish is seeded with cells and the cells are incubated in growth medium for about 18–24 hours prior to treatment with different concentrations of the nucleic acid sequence-modifying agent. Treated cells are washed with phosphate buffered saline and further incubated in culture medium. An increase in the number of treated cells following incubation in culture medium as compared to the number of cells at the time of treatment indicates that the concentration of the nucleic acid sequence-modifying agent is non-toxic. Also, the ability of treated cells to regenerate multicellular organisms may readily be determined using methods known in the art which depend on the type of treated cell used (described infra).

2. Accessing Clones In the Library

The Library which is generated following treatment of cells with the nucleic acid sequence-modifying agent provides a database of genomic sequences. The Library contains a pool of clones, each clone containing a unique set of genomic modifications.

The pool of clones in the Library may be arrayed as single clones. One of skill in the art appreciates that the number of clones may be governed by the estimated number of genes in the genome of the treated cells. For example, the genome of mouse ES cells contains approximately 100,000 genes. Thus, approximately 500,000 individual clones from the Library may be arrayed using, for example, one thousand 96-well microtiter dishes.

Cells from the arrayed Library may be replica plated and cells from one set of replica plates frozen (i.e., to generate a master set) for future recovery of viable modified cells. Another set is screened for the presence of the modified gene of interest using any one of a number of methods known in the art.

For example, the modification in the gene of interest may be determined by amplification of the modified gene of interest by, for example, the polymerase chain reaction using primers which are specific for the modified gene of interest, coupled with sequencing of the PCR-amplified sequence.

The term "amplifying" and its grammatical equivalents are defined as the production of additional copies of a nucleic acid sequence and is generally carried out using polymerase chain reaction technologies well known in the art [Dieffenbach CW and GS Dveksler (1995) PCR Primer, a Laboratory Manual, Cold Spring Harbor Press, Plainview N.Y.]. As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). For example, the PCR amplified fragments may then be analyzed for the presence of mutations in the gene of interest using a variety of techniques, e.g., nucleotide sequencing, SSCP, etc. [see, e.g., Greenman et al. (1998) Genes, Chromosomes & Cancer 21:244–249]. Briefly, The gene of interest is amplified by PCR using radioactive primers. PCR-amplified sequences are separated by gel electrophoresis, and the gels are dried and autoradiographed. The patterns of migrating PCR-amplified bands from modified cells and control cells (i.e., cells which had not been treated with the nucleic acid sequence-modifying agent) are compared. Differences in the patterns of migrating PCR-amplified bands indicates the presence of at least one modification in the PCR-amplified gene of interest.

Once a positive individual clone is identified, the type and location of the modification caused by the nucleic acid sequence-modifying agent in the gene of interest is determined by sequencing the gene of interest in the clone and comparing the sequence from the clone with the wild-type sequence of the gene of interest. Sequencing nucleic acid sequences is within the skill of the art and may be accomplished by, for example, using commercially available automated sequencers such as ABI 373 DNA sequencer using "GENESCAN 672" software.

3. Determining Gene Function

The allelic series of modifications in the genomic sequence of interest may be used to determine the function of the genomic sequence by, for example, determining the effect of the allelic modifications in cultured cells or in multicellular organisms which are generated to contain one or more of the allelic modifications as described below.

A. Cultured Cells

Cells from the Library which contain at least one modification in the gene of interest may be used either directly or indirectly to determine the function of the gene of interest. For example, a clone of cells from the Library may be directly cultured in order to determine the function of the genomic sequence in that cell (e.g., by determining biochemical, molecular biological, and/or morphological changes in the cultured clone). This approach is most useful in evaluating the phenotype of dominant mutations in the cells. The function of recessive mutations in a gene of interest may be determined by generating cells which are homozygous or hemizygous with respect to the gene of interest using methods known in the art.

B. Regenerating Muticellular Organisms

In a preferred embodiment, where the cloned cell which contains the modified gene of interest is a cell (e.g., fertilized egg cell, ES cell, etc.) capable of regenerating a multicellular organism, the function of the gene may be evaluated by passing the modification through the germline of a non-human organism gene rated from the cloned cell using methods known in the art.

For example, where the cell treated with the nucleic acid sequence-modifying agent is a fertilized egg cell of a mammal, transgenic mammals are generated by implanting the treated fertilized egg cell into the uterus of a pseudopregnant female and allowing the cell to develop into an animal. This method has been successful in producing transgenic mice, sheep, pigs, rabbits and cattle [Jaenisch (1988) supra; Hammer et al., (1986) J. Animal Sci.:63:269; Hammer et al., (1985) Nature 315:680–683; Wagner et al., (1984) Theriogenology 21:29].

Additionally, where the fertilized egg cell which is treated with the nucleic acid sequence-modifying agent is derived from a fish (e.g., zebrafish), transgenic zebrafish may be generated by allowing the fertilized egg cell to develop without the need for attention from its parents. Development of a fully developed zebrafish from a fertilized egg occurs over a 96 h period of time during which time the developing embryo is transparent, thus facilitating observation of its tissues and organs. Following completion of embryogenesis over a 96 h period, sexually mature adult zebrafish may develop at the age of two-months, depending on their nutritional condition. The well characterized zebrafish developmental periods and events occurring therein facilitate the detection of alterations in these events by modifications to the gene of interest, thus allowing a determination of gene function.

Alternatively, where the cell treated with the nucleic acid sequence-modifying agent is a ES cell, multicellular organisms may be generated by introducing the modified ES cell back into the embryonic environment for expression and subsequent transmission to progeny animals. The most commonly used method is the injection of several ES cells into the blastocysts cavity of intact blastocysts [Bradley et al., (1984) Nature 309:225–256). Alternatively, a clump of ES cells may be sandwiched between two eight-cell embryos [Bradley et al., (1987) in "Teratocarcinomas and Embryonic Stem Cells: A Practical Approach," Ed. Robertson E. J. (IRL, Oxford, U.K.), pp. 113–151; Nagy et al., (1990) Development 110:815–821]. Both methods result in germ line transmission at high frequency.

While it is preferred that the multicellular organisms generated from the cells which are treated with the nucleic acid sequence-modifying agent are transgenic organisms (i.e, organisms which contain a transgene in a germ-line cell), the invention also expressly contemplates chimeric organisms (i.e., organisms which contain a transgene in only somatic cells).

The regenerated animals, whether heterozygous or homozygous for a modification in a gene of interest, and whether they contain a modified gene of interest in a somatic and/or germline cell, may be used to determine the function of the gene of interest. For example, morphological and pathological changes relative to wild-type animals may be determined using methods known in the art such as by visual inspection, histological staining, electron microscopy, magnetic resonance imaging (MR), computerized tomography (CT) scans and the like. Morphological changes as a result of the modification in the gene of interest indicate that the gene which is modified by the nucleic acid sequence-modifying agent is important in the formation of the structure whose morphology is altered by the gene modification.

Alternatively, changes may be biochemical. Biochemical changes may be determined by, for example, changes in the activity of known enzymes, or in the rate of accumulation or utilization of certain substrates, etc. Such changes in response to modification of the gene suggest that the gene product acts in the same pathway as the enzymes whose activity is altered, or in a related pathway which either supplies substrate to these pathways, or utilizes products generated by them.

Yet another alternative is the determination of behavioral changes in an organism. Where the organism is unicellular e.g. yeast cell, or bacterium, such changes may include light tropism, chemical tropism and the like, and would suggest that the gene of interest regulates these events. Where behavioral changes are observed in a multicellular organism, e.g., loss of spatial memory, aggressiveness, etc., such changes indicate that the gene of interest functions in a neural pathway involved in controlling such behavior.

Other changes include molecular biological changes, e.g. in the levels of expression of genes as determined by, for example, subtraction hybridization. Such changes suggest that the gene which is modified by the nucleic acid sequence-modifying agent encodes a transcriptional regulatory molecule such as a transcription factor.

Experimental

The following examples serve to illustrate certain preferred embodiments and aspects of the present invention and are not to be construed as limiting the scope thereof.

EXAMPLE 1

N-ethyl-N-nitrosurea-Induced Mutations in the Hypoxanthine Phosphoribosyl Transferase (Hprt) Gene Of Mouse Embryonic Stem Cells This experiment was carried out in order to determine whether N-ethyl-N-nitrosurea (ENU) induces mutations in the hypoxanthine guanine phosphoribosyltransferase (Hprt) gene in mouse embryonic stem (ES) cells which result in inactivation of the encoded enzyme. The rates of spontaneous mutations and of mutations caused by treatment of the ES cells with different concentrations of ENU were compared as follows.

Mouse ES cells (129/Sv+$^{Tyr}$, +$^P$) were used. Cells were grown in culture medium [MEM (Gibco) supplemented with 15% heat-inactivated fetal calf serum, LIF, and 10 $\mu$M β-mercaptoethanol. Cells were routinely grown on 100-mm petri dishes and cultivated at 37° C. in a humidified atmosphere of 5% $CO_2$ in air. For subculturing, cells were disassociated with HBSS containing 0.25% trypsin and 0.02% EDTA. After a 3-minute incubation at room temperature, cells were resuspended in culture medium and cell numbers determined using a hemocytometer.

The plating efficiency was determined by plating $2 \times 10^3$ cells per 100-mm dish, fixing the cells after 6-days with methanol, staining with 0.01% crystal violet and scoring colonies. Colonies were scored for the calculation of plating efficiency as percent of the inoculated cell number. The plating efficiencies were approximately 20%.

The spontaneous frequency of mutations which inactivated Hprt was determined by trypsinizing actively growing ES cells (i.e., 3 days following subculture) as described above, seeding duplicate 100-mm petri dishes with $1 \times 10^6$ cells, and culturing the cells in culture medium containing 10 $\mu$M 6-thioguanine (6-TG). The number of surviving colonies after 7 days of culture was one colony per plate, i.e., the spontaneous mutation frequency at the Hprt locus (taking into account plating efficiency) was 1/400,000 cells.

The frequency of ENU-induced mutations which inactivate Hprt in ES cells was determined using two protocols as follows.

A. Protocol 1

In the first protocol, actively growing ES cells were trypsinized and plated at $5 \times 10^5$ cells per T25 flask and after 1 day preincubation treated for 5 hours with 0.3 mg/ml, 0.4 mg/ml or 0.5 mg/ml ENU (dissolved in medium without FCS by vigorous shaking and filter sterilization with 0.2 $\mu$m cellulose acetate filters immediately before use). Control cells and cells which had been treated with ENU were washed three times with PBS and the number of surviving cells determined after 3 days of culture in culture medium by plating 2,000 cells from control and from ENU-treated flasks and counting surviving colonies as described above. Treatment with 0.3 mg/ml, 0.4 mg/ml and 0.5 mg/ml ENU resulted in 10%, less than 5% and 0% survival, respectively. Surviving EA cells which had been treated with 0.3 mg/ml ENU were subcultured at 3:1 onto 60-mm petri dishes in the presence (set 1) and absence (set 2) of primary embryothic fibroblasts (PMEFs). ES cells grown on PMEFs (set 1) were cultured for 3 days, subcultured at 3:1 onto 60-mm petri dishes without PMEFs, trypsinized, plated at $4 \times 10^5$ cells per 100-mm plate without PMEFs and grown for 2 days. ES cells grown in the absence of PMEFs (set 2) were trypsinized-after 5 days in culture and plated at $4 \times 10^5$ cells per 100-mm plate without PMEFs. Cells (set 1 and set 2) were subsequently grown for 1 day prior to the addition of 10 μM 6-TG to the culture medium and further incubated for an additional 6 days in the presence of 6-TG. The number of 6-TG resistant colonies was calculated, and individual colonies were separately plated in a 96-well microtiter dish. The results are shown in Table 1.

TABLE 1

Colonies Surviving 6-TG selection (Hprt deficient)

| Plate No. | No. Surviving Colonies (+PMEF plates) | No. Surviving Colonies (−PMEF plates) |
|---|---|---|
| 1 | 3 | 12 |
| 2 | 2 | 9 |
| 3 | 6 | 15 |
| 4 | 3 | 12 |
| 5 | 2 | 14 |
| 6 | 5 | 15 |
| Total colonies | 21 | 77 |
| Total No. cells plated | $24 \times 10^3$ | $24 \times 10^3$ |
| Plating Efficiency (20%) | $48 \times 10^4$ | $48 \times 10^4$ |
| ENU survival (10%) | $48 \times 10^3$ | $48 \times 10^3$ |

TABLE 1-continued

Colonies Surviving 6-TG selection (Hprt deficient)

| Plate No. | No. Surviving Colonies (+PMEF plates) | No. Surviving Colonies (−PMEF plates) |
|---|---|---|
| Mutation Frequency | | |
| Minimum | 1/8,000 | 1/8,000 |
| Maximum | 1/2,000 | 1/623 |

The results in Table 1 show that ENU induces mutations in the Hprt gene of mouse ES cells at a frequency which is from 5-fold to 650-fold greater than the rate of spontaneious mutation in the Hprt gene. The mutatin frequency could not be more accurately determined since ENU-treated cells were trypsinized and replated before selection was started, thus reslting in loss of clonality, and estimation of only a range of mutation frequency.

B. Protocol 2

In the second protocol, actively growing ES cells were trypsinized and plated at two densities ($1 \times 10^5$ and $0.5 \times 10^5$ cells/well) in 24-well tissue culture plates instead of T25 flasks. After a one-day preincubation period, cells were treated for 5 hours with 0.3 mg/ml or 0.4 mg/ml ENU (as described above) and subsequently treated as described in Table 2.

TABLE 2

Protocol for Treating ES Cells with ENU

| | 0.3 mg/ml ENU | | 0.4 mg/ml ENU | |
|---|---|---|---|---|
| Days after plating | Plate 1 | Plate 2 | Plate 3 | Plate 4 |
| 5 | Split 1:3. Passed one-third to new well, discarded remaining two-thirds. | | Discarded, very few colonies surviving | |
| 6 | | split 1:3 | | |
| 7 | | | | split 1:2 |
| 9 | Plated one-third of each well onto separate 60-mm dishes | Plated half of each well onto separate 60-mm dishes | | |
| 10 | Added 6-thioguanine | Added 6-thioguanine | | Plated half of each well onto separate 60-mm dishes |
| 16 | 9 plates yielded colonies, 15 plates had no colonies No. colonies/plate Plate 1: 1 colony Plate 2: 3 colonies Plate 3: 5 colonies Plate 4: 4 colonies Plate 5: 1 colony Plate 6: 1 colony Plate 7: 2 colonies Plate 8: 2 colonies Plate 9: 4 colonies Total: 23 colonies | 6 plates yielded colonies, 18 plates had no colonies No. colonies/plate Plate 1: 2 colonies Plate 2: 1 colony Plate 3: 2 colonies Plate 4: 1 colony Plate 5: 4 colonies Plate 6: 2 colonies Total: 12 colonies | | |
| 17 | | | | 2 plates yielded colonies, 22 plates had no colonies No. colonies/plate Plate 1: 14 colonies Plate 2: 18 colonies Total: 22 colonies |
| Total No. cells plated | $2.4 \times 10^5$ | $1.2 \times 10^5$ | NA | $1.2 \times 10^5$ |

TABLE 2-continued

Protocol for Treating ES Cells with ENU

| Days after plating | 0.3 mg/ml ENU | | 0.4 mg/ml ENU | |
|---|---|---|---|---|
| | Plate 1 | Plate 2 | Plate 3 | Plate 4 |
| Plating efficiency (20%) | 4.8 × 10³ | 2.4 × 10³ | | 2.4 × 10³ |
| ENU survival (10%) | 4.8 × 10⁴ | 2.4 × 10⁴ | | 2.4 × 10⁴ |
| Mutation frequency | | | | |
| minimum | 1/5,000 | 1/3,000 | | 1/9,000 |
| maximum | 1/2,000 | 1/1,500 | | 1/800 |

[1]By plating the cells into 24 well plates prior to ENU treatment, more individual populations were tested yielding approximately the same mutation frequency as in the first protocol (i.e., from about 1/600 to about 1/9,000).

These results establish that ENU induces mutations in the Hprt gene at a frequency of from about 1/600 to about 1/9,000. The frequency of mutaions induced by ENU at somatic genes is expected to be higher than the experimentally determined frequency of 1/600 since the above experimental design selects for cells which are deficient in HPRT activity, thus failing to detect Hprt mutations that result in little or no change in enzyme activity. Furthermore, the frequency of chemically-induced mutaions at the Hprt gene have been found in mammalian cell specific-locus mutation assays to be lower than the frequency at other genes, e.g., the tk +/−.

EXAMPLE 2

Generating An Allelic Series Of Mutations In The PKD2 Gene of Mouse Embryonic Stem Cells Using Methyl Methane Sulfonate This Example describes the generation of a Library of mouse ES cells which contain an allelic series of mutations generated by treatment with methyl methane sulfonate and the screening of the PKD2 gene in the Library.

1 Preparing a Library of MMS-treated mouse ES cells

Actively growing mouse ES cells (129/Sv+$^{Tyr}$, +$^P$) which are grown and subcultured as described above (Example 1) are plated at two densities (1×10⁵ and 0.5×10⁵ cells/well) in 24-well tissue culture plates. After 1 day of preincubation in culture medium, cells are treated for one hour with 0.5 mM to 1.5 mM MMS. Surviving cells are counted and individual clones are picked and plated in 96-well microtiter dishes.

2. Screening The Library for PKD2 Alleles

Genomic DNA is isolated from MMS-treated and control (i.e., receiving no MMS) mouse ES cells using methods known in the art and the isolated genomic DNA is screened for mutations using PCR in combination with SSCP as previously described [Veldhuisen et al. (1997)]. Briefly, approximately 30 ng genomic DNA is amplified in a total volume of 15 μl by using a primer pair which is selected to amplify exon 1 [forward primer: (SEQ ID NO:1) 5'-AGGGAGGTGGAAGGGGAAGAA-3'; reverse primer: (SEQ ID NO:2) 5'-TTCTGGTTCGTGCATCTGCC-3'] of the PKD2 gene (expected product size is 335 bp), in the presence of 0.2 mM each of dGTP, DATP, and dTTP and 0.025 mM α-$^{32}$P-dCTP, 0.06 Units Supertruper polymerase (HT Biotechnology) in PCR buffer (0.1 M Tris-HCl pH 9.0, 0.5 M KCl, 0.1% gelatin, 1.5 mM MgCl$_2$, and 1% Triton X-100. Denaturation is for 2 min at 94° C., followed by 30 cycles of 1 min at 94° C., 2 min at 63° C., and 1 min at 72° C. and then a final extension for 9 min at 72° C. The PCR products are diluted 1:5 in SSCP loading buffer (47.5% formamide, 15 mM EDTA, 0.05% SDS, 0.05% xylene cyanole, and 0.05% bromophenol blue) and are denatured at 95° C. The PCR-amplified products are separated on 5% nondenaturing polyacrylamide gels with or without 10% glycerol at either room temperature or 4° C. Gels are exposed to Kodak XAR5 films. The pattern of radioactive bands is compared between MMS-treated and control embryos. Differences in the pattern of PCR-amplified sequences obtained from control and MMS-treated cells indicate the presence of mutations in the PCR-amplified sequences. The type and location of these mutations is determined by DNA sequencing.

3. DNA Sequencing

Sequencing is performed with the Automated Laser Fluorescent DNA sequence (ALF Pharmacia). Products for the ALF are obtained by amplification of genomic DNA by use of the forward and reverse primers described supra, with an M13 extension (SEQ ID NO:3) 5'-CGACGTTGTAAAACGACGGCCAGT-3' at the 5' end of the forward primer and with a biotin label at the 5' end of the reverse primer. The PCR products are purified by use of an obtained using magnetic beads (Dynabeads). The sequence reaction is performed with a fluorescent universal or reverse primer of the autoread kit (Pharmacia).

EXAMPLE 3

Generating An Allelic Series Of Mutations in the BRCA1 Gene of Mouse Embryonic Stem Cells Using N-methyl-N'-nitro-N-nitrosoguanidine This Example describes the generation of a Library of mouse ES cells which contain an allelic series of mutations generated by treatment with N-methyl-N-nitro-Nd nitrosoguanidine (MNNG), and the screening of the BRCA1 gene in the Library.

1. Preparing a Library of MNNG-treated mouse ES Cells

Actively growing mouse ES cells (129/Sv+$^{Tyr}$, +$^P$) which are grown and subcultured as described above (Example 1) are plated at two densities (1×10⁵ and 0.5×10⁵ cells/well) in 24-well tissue culture plates. After 2 days of preincubation in culture medium, cells are treated for 0.75 hours with 1–10 μMMNG. Surviving cells are counted after 2 days in culture. Individual clones are picked and plated in 96-well microtiter dishes.

2. Screening And Sequencing The Library For BRCA1 Alleles

Genomic DNA is isolated from MNNG-treated cells and control cells (i.e., cells which are not treated with MNNG) using methods known in the art. Isolated genomic DNA is screened for mutations using PCR in combination with SSCP as previously described [Greenman et al. (1998)].

Briefly, primer sequences for exon amplification from genomic DNA are obtained form the ftp file at morgan.med.utal.edu [Miki et al. (1994) Science 266:66–71] except for primers for exons 6 and 7 [Friedman et al. (1994) Nat. Genet. 8:399–404]. Reverse primers are biotinylated at the 5' end for solid-phase sequencing. Exons 2–3, 5–10 and 12–24 are amplified by PCR, and PCR-amplified products are electrophoresed using two conditions for gel electrophresis since this has been reported to increase the sensitivity of mutation detection. The first condition uses 8% polyacrylamide, 0.16% bis-acrylamide, 5% glycerol, in 1×Tris-borate-EDTA (TBE) buffer. The second condition uses 0.5×MDE gels (JT Baker Inc., Phillipsburg, N.J.), 10% glycerol in 0.6×TBE buffer. The 8% acrylamide and 0.5%× MDE gels are electrophoresed in 1×TBE and 0.6×TBE buffer, respectively, at 6 to 9 W, for 16–20 hours at 4° C. Gels are dried under vacuum at 80° C. and autoradiographed at room temperature for one to four days. The pattern of PCR-amplified sequences from control and MNNG-treated cells is compared; differences in the pattern indicate the presence of mutations in the PCR-amplified sequences. The type and location of these mutations is determined by DNA sequencing as described supra (Example 2).

Alternatively, genomic DNA is screened for mutations using fluorescent chemical cleavage of mismatch (FCCM) since this method has been reported to detect mutations in addition to those detected by SSCP [Greenman et al. (1998)]. To detect mutations in exon 11, exon 11 is amplified as three overlapping PCR products (1322 bp, 1519 bp, and 1369 bp). Each of the six primers is synthesized to generate an unmodified set and a set which is biotinylated at the 5' end. Genomic DNA is amplified with biotinylated primers, and probed with the unmodified primers. Chemical cleavage is carried out with hydroxylamine or osmium tetroxide modification and piperidine cleave. The products are loaded on a 5% polyacrylamide/urea gel on the ABI 373 DNA sequence and electrophoresed at 40 W for 14 hours. Data is collected and analyzed using Genescan 672 software. Differences between the sequence of PCR-amplified BRCA1 which is derived from MNNG-treated cells and from control cells are used to determine the type and location of mutations introduced by MNNG.

From the above, it is clear that the invention provides methods for determining gene function which may efficiently be applied on a genome-wide scale, which generate more than one mutation in a gene of interest, and which do not only abrogate the function of the gene.

All publications and patents mentioned in the above specification are herein incorporated by reference. Various modifications and variations of the described method and system of the invention will be apparent to those skilled in the art without departing from the with specific preferred embodiments, it should be understood that the invention as claimed should not be unduly limited to such specific embodiments. Indeed, various modifications of the described modes for carrying out the invention which are obvious to those skilled in the art and related fields are intended to be within the scope of the following claims.

What is claimed is:

1. A method of producing an allelic series of modifications in a gene of interest in a cell, comprising:
    a) providing:
        i) an in vitro culture comprising between 200 and 600 isolated mouse embryonic stem cells, each of said cells comprising a gene of interest;
        ii) a chemical agent capable of producing at least one modification in said gene of interest;
    b) treating said mouse embryonic stem cells with said chemical agent under conditions such that (i) it is at least 70% probable that at least one modification in every gene in said mouse embryonic stem cells is produced, and ii) a mixture of embryonic stem cells comprising said gene of interest is produced, said mixture of embryonic stem cells comprising embryonic stem cells having a first modification in said gene of interest, and embryonic stem cells having a second modification in said gene of interest; and
    c) isolating said embryonic stem cells having a first modification in said gene of interest and said embryonic stem cells having a second modification in said gene of interest, thereby producing an allelic series of modifications in said gene of interest in the isolated embryonic stem cells.

2. The method of claim 1, wherein said treating is under conditions such that it is at least 85% probable that at least one modification in every gene in said mouse embryonic stem cells is produced.

3. The method of claim 1, wherein said treating is under conditions such that it is at least 95% probable that at least one modification in every gene in said mouse embryonic stem cells is produced.

4. The method of claim 1, further comprising step d) placing at least one embryonic stem cell selected from the group consisting of said embryonic stem cells having a first modification in said gene of interest and said embryonic stem cells having a second modification in said gene of interest into an environment under conditions so as to generate a mouse comprising a modification selected from the group consisting of said first modification in said gene of interest and said second modification in said gene of interest.

5. The method of claim 1 wherein said gene of interest is associated with a disease.

6. The method of claim 5, wherein said gene of interest is selected from the group consisting of the p53 gene, BRCA1 gene, PKD1 gene, PKD2 gene, and PKD3 gene.

7. The method of claim 1, further comprising step d) detecting at least one of said first and second modification in said gene of interest using fluorescent chemical cleavage of mismatch.

* * * * *